US008450072B2

(12) United States Patent
Dodds (10) Patent No.: US 8,450,072 B2
(45) Date of Patent: *May 28, 2013

(54) MULTI-STAGE NUTRIGENOMIC DIAGNOSTIC FOOD SENSITIVITY TESTING IN ANIMALS

(76) Inventor: W. Jean Dodds, Santa Monica, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/960,031

(22) Filed: Dec. 3, 2010

(65) Prior Publication Data

US 2011/0111415 A1 May 12, 2011

Related U.S. Application Data

(63) Continuation of application No. 12/995,037, filed as application No. PCT/US2010/020677 on Jan. 11, 2010, which is a continuation-in-part of application No. 12/545,041, filed on Aug. 20, 2009, now Pat. No. 7,892,763, and a continuation-in-part of application No. 12/465,603, filed on May 13, 2009, now Pat. No. 7,867,720.

(60) Provisional application No. 61/147,443, filed on Jan. 26, 2009.

(51) Int. Cl.
*G01N 33/53* (2006.01)

(52) U.S. Cl.
CPC .............. *G01N 33/53* (2013.01); *Y10S 436/811* (2013.01)
USPC ............ 435/7.1; 435/7.92; 436/513; 436/811

(58) Field of Classification Search
None
See application file for complete search history.

(56) References Cited

U.S. PATENT DOCUMENTS

| | | | |
|---|---|---|---|
| 4,110,476 A * | 8/1978 | Rhodes | 426/41 |
| 4,414,240 A * | 11/1983 | Lee | 426/614 |
| 4,487,830 A * | 12/1984 | Coates et al. | 435/7.23 |
| 6,287,254 B1 | 9/2001 | Dodds | |
| 6,493,641 B1 * | 12/2002 | Singh et al. | 702/32 |
| 6,537,213 B2 | 3/2003 | Dodds | |
| 6,689,569 B2 | 2/2004 | Vojdani | |
| 6,730,023 B1 | 5/2004 | Dodds | |
| 6,858,398 B2 | 2/2005 | Vojdani | |
| 7,029,441 B2 | 4/2006 | Dodds | |
| 7,134,995 B2 | 11/2006 | Dodds | |
| 7,296,537 B2 | 11/2007 | Burghardi et al. | |
| 7,867,720 B2 * | 1/2011 | Dodds | 435/7.1 |
| 7,892,763 B2 * | 2/2011 | Dodds | 435/7.1 |
| 2002/0022772 A1 | 2/2002 | Dodds | |
| 2003/0135096 A1 | 7/2003 | Dodds | |
| 2003/0233984 A1 | 12/2003 | van de Ligt et al. | |
| 2005/0090718 A1 | 4/2005 | Dodds | |
| 2005/0255533 A1 | 11/2005 | Dantini et al. | |
| 2006/0045909 A1 | 3/2006 | Friesen et al. | |
| 2006/0200320 A1 | 9/2006 | Al-Murrani | |
| 2007/0118295 A1 * | 5/2007 | Al-Murrani | 702/19 |
| 2009/0132465 A1 | 5/2009 | Dodds | |

FOREIGN PATENT DOCUMENTS

WO  WO 99-67642 A2  12/1999
WO  WO 2010/085387 A2  7/2010

OTHER PUBLICATIONS

Cave et al., Evaluation of the immunogenicity of dietary proteins in cats and the influence of the canning process, American Journal of Veterinary Research, vol. 65, No. 10, Oct. 2004, pp. 1427-1433.*
Harley et al., Determination of salivary and serum immunoglobulin concentrations in the cat, Veterinary Immunology and Immunopathology 65 (1998), pp. 99-112.*
Flickinger, et al.; Immunoglobulin A Concentrations in Adult Dogs Vary According to Sample Type and Collection Time and Method; Waltham International Science Symposium: Nature, Nurture, and the Case for Nutrition; J. Nutr. 134: 2130S-2132S, 2004; © 2004 American Society for Nutritional Sciences; Department of Animal Sciences, University of Illinois, Urbana, IL 61801.
Rinkinen, et al.; Relationship between canine mucosa and serum immunoglobulin A (IgA) concentrations: serum IgA does not assess duodenal secretory IgA; PubMed; 2003; 47(2): 155-9; U.S. National Library of Medicine National Institutes of Health; Department of Clinical Veterinary Sciences, Faculty of Veterinary Medicine, Helsinki University, P.O. Box 57, 00014; http://www.ncbi.nlm.nih.gov/pubmed/12680719.
German, et al.; Measurement of IgG, IgM and IgA concentrations in canine serum, saliva, tears and bile; Veterinary Immunology and Immunopathology; 1998; 107-121; Department of Clinical Veterinary Science, University of Bristol, Langford, Bristol BS40 5DU, UK; Department of Pathology and Microbiology, University of Bristol, Langford, Bristol BS40 5DU, UK.
Heddle, et al.; I. Immunochemical Characterization of Dog Serum, Parotid Saliva, Colostrum, Milk and Small Bowel Fluid; Dog Immunoglobulins; 1975; 185-195; 29; Department of Microbology, The University of Adelaide, Adelaide, Australia.
Tizard, Ian; Antibodies; Veterinary Immunology an Introduction; 1992; 115; Fourth Edition; W.B. Saunders Company, Harcourt Brace Jovanovich, Inc., Philadelphia, London, Toronto, Montreal, Sydney, Tokyo.

(Continued)

*Primary Examiner* — Gary W Counts
(74) *Attorney, Agent, or Firm* — Greenberg Traurig, LLP (57) ABSTRACT

A multi-stage method for diagnosing an immunologic food sensitivity or intolerance in a companion animal. Firstly a saliva or blood spot or other non-serum bodily fluid sample is collected. The screening the saliva or blood spot or other non-serum bodily fluid sample detects the presence of at least one of IgA or IgM antibody to a particular food ingredient or composition. An immunologic food sensitivity or intolerance based on the presence of the antibody is diagnosed. Secondly a blood sample is collected and serum from the sample is screened to detect the semi-quantitative or quantitative presence of at least one of an IgA, IgM or IgG antibody or immune complex to a particular food ingredient or composition. An immunologic food sensitivity or intolerance based on the presence of the antibody or immune complex is diagnosed. Thirdly, a biologically active nutrient in relation to the animal from a molecular dietary signature is determined. The molecular dietary signature for the animal is a variation of expression of a set of genes, proteins or metabolites which may differ for the genotype of each animal.

7 Claims, 2 Drawing Sheets

OTHER PUBLICATIONS

Delacroix, et al.; Quantitative Relationships of Monomeric and Polymeric Immunoglobulin A, Immunoglobulin M, and Other Proteins in Serum, Bile, and Saliva; Selective Transport of Polymeric Immunoglobulin A in Bile; Aug. 1982; 230-241; vol. 70; J. Clin. Invest. © The American Society for Clinical Investigation, Inc.

Tizard, Ian; Immunity at Body Surfaces; Veterinary Immunology an Introduction; 1992; 242; Fourth Edition; W.B. Saunders Company, Harcourt Brace Jovanovich, Inc., Philadelphia, London, Toronto, Montreal, Sydney, Tokyo.

M.F. Bottcher, M.F. et al., (Total and allergen-specific immunoglobulin A levels in saliva in relation to the development of allergy in infants up to 2 years of age) Clin. Exp. Allergy Sep. 2002, vol. 32, No. 9, pp. 1293-1298.

Foster, A.P. et al. "Serum IgE and IgG Responses to Food antigens in Normal and Atopic Dogs, and Dogs with Gastrointestinal Disease" Vet. Immunol. Immunopathol. May 2003, vol. 92, No. 3-4, pp. 113-124.

Day, M.J. et al. "The Canine Model of Dietary Hypersensitivity" Proc. Nutr. Soc. Nov. 2005, vol. 64, No. 4, pp. 458-464.

* cited by examiner

FIG. 2

MULTI-STAGE NUTRIGENOMIC DIAGNOSTIC FOOD SENSITIVITY TESTING IN ANIMALS

RELATED APPLICATIONS

This application claims priority from International patent application Ser. No. PCT/US10/020677, filed Jan. 11, 2010, and which is a Continuation in Part of application Ser. No. 12/545,041 filed Aug. 20, 2009, now U.S. Pat. No. 7,892,763, entitled MULTI-STAGE NUTRIGENOMIC DIAGNOSTIC FOOD SENSITIVITY TESTING IN ANIMALS (Dodds), and which claims the benefit of priority of earlier filed U.S. applications. This application is also a Continuation-in-Part of application Ser. No. 12/465,603, filed May 13, 2009, now U.S. Pat. No. 7,867,7206, entitled FOOD SENSITIVITY TESTING IN ANIMALS (Dodds), which claims the benefit of and priority to U.S. Provisional Application Ser. No. 61/147,443, filed Jan. 26, 2009, entitled FOOD SENSITIVITY TESTING IN ANIMALS (Dodds). This application is concerned with and relates to the disclosure of application Ser. No. 12/316,824, filed Dec. 16, 2008, now U.S. Pat. No. 7,873,482, entitled DIAGNOSTIC SYSTEM FOR SELECTING NUTRITION AND PHARMACOLOGICAL PRODUCTS FOR ANIMALS. The contents of all of these applications are incorporated by reference herein in their entirety.

BACKGROUND

The disclosure is directed to food sensitivity testing in companion animals. This disclosure is also concerned with animal nutrition diagnosis. More particularly the disclosure is directed to the testing and diagnosis of genetic issues relating to nutrition issues and disorders of companion animals, for instance dogs and cats.

More specifically the disclosure is directed to animal nutrition diagnosis and care, animal well-being and nutrition, and methods and systems for enhanced determination of these factors.

A common health concern identified by health surveys of several purebred dog clubs is food sensitivity or intolerance. Other than time-consuming feeding trials, which eliminate potential allergic ingredients every several weeks, testing for this disorder uses expensive and unsightly skin patch testing or serum allergy screening that lack specificity.

Delayed food sensitivities in people are extremely common and can be manifested by gastrointestinal, neurological, pulmonary, dermatologic, ear, nose and throat, musculoskeletal, genitourinary, cardiovascular and endocrine problems. Similar clinical problems are manifested in animals with food sensitivities.

Diagnostic testing systems available for humans are typically based on either immunoglobulin E (IgE) or immunoglobulin A (IgA) or a combination of immunoglobulin G (IgG) antibody or immune complex testing mediated by complement.

The newer test methodologies for humans are run on serum, feces, or saliva and typically use ELISA or other immunoassay platforms such as lateral flow, or latex or bead agglutination, and identify IgG or IgA or immune complex reactions to food ingredients that are mediated by complement, as well as IgA or immunoglobulin M (IgM) antibodies to food ingredients that are elaborated in saliva.

Research has shown that the key to delayed or latent or pre-clinical food sensitivity testing in humans is the identification of the offending IgG or IgA antibodies and immune complexes in serum or feces, and the offending IgA or IgM antibodies in saliva. In fact, antibodies to food ingredients can appear in the saliva before the clinical or gastrointestinal biopsy diagnosis of inflammatory bowel disease or "leaky gut syndrome" is made in human patients. Saliva testing can thus reveal the latent or pre-clinical form of food sensitivity. A similar elaboration of IgA or IgM antibody in saliva but not serum pertains to animals with latent or pre-clinical gastrointestinal disease.

Delayed sensitivities in humans are usually revealed as soon as 2 hours or as long as 72 hours after eating, which is the reason it can be difficult to connect the symptoms with a food or foods eaten as long as several days previously. There is a very high correlation between delayed food sensitivity and the amount and frequency of the food consumed.

In human serum testing, food sensitivity reactions in the gut lead to increased blood levels of IgA or IgG directed to these food ingredients. Similarly, the immune complexes being formed from food reactions in the blood adhere to red blood cells and these altered blood cells are then cleared by the body's recticuloendothelial system in the liver and spleen. Individuals having more immune complex on their red blood cells are the ones who suffer from chronic food sensitivities.

In saliva testing, deposition of food antigens or peptides in the gut has been documented in humans to lead to the production of IgA or IgM antibodies in the serum and in secretions such as saliva. In some situations, IgA or IgM antibodies to food ingredients appear in saliva but are not present in serum. So in humans salivary antibodies serve as an indication of a general mucosal immune response and can be induced in people and animals without parallel antibodies being detected in serum.

There is a need to provide for practical and rapid screening or testing for food sensitivity and intolerance to permit enhancement of the health of animals.

Studies have indicated that specialized nutrient intake extends and improves life, delays onset and slows progression of disease, and enhances the quality of life of companion animals.

Changing the proportions of macro-nutrients and micro-nutrients in different nutrient and food products is important in obtaining the right balance. To date, the utility of such characteristics and components has been limited or not as useful as possible.

Currently, time consuming elimination dietary trials are done where one ingredient at a time is removed and the remaining diet is fed for six to eight weeks to determine if the animal patient's food sensitive or food intolerance symptoms subside. Alternatively, arbitrary selection can be made of a food preparation containing limited, namely restricted antigen source, or novel, namely not fed previously, ingredients(s) are employed. Both these techniques are imprecise or indirect methods of addressing the problem.

The present disclosure provides for screening or testing animal subjects for sensitivity or intolerance relative to dietary compositions, and the testing and screening should be advantageous and commercially useful.

There is also a need to conduct periodic comprehensive nutrition assessments of animals.

The probability that an individual animal will develop a specific nutrition-related condition in its lifetime is a product of complex interactions between its genetic makeup, environmental influences including diet, and agents of disease (e.g., chemical, physical, or biological) that the animal encounters.

More specifically, it is necessary in animal nutrition diagnosis and care for comprehensive nutrition assessments of animals for diseases and disorders of animals be achieved in order to reduce morbidity and mortality, and improve the quality of life and lifespan.

It is important for nutritionists or other animal food professionals to prescribe or recommend nutrient needs or diets on the basis of more precise knowledge of how nutrients or food components interact at the level of the genome, where these constituents act by "up- or down-regulating" a set of target genes. Animal nutritionists or other animal food professionals should design nutrients or foods tailored to the genome or genomic profile or to prescribe or recommend the inclusion of specific molecules in the diets of animals to optimize physiological homeostasis, disease prevention and treatment, and productive or reproductive performances. Individualized nutrition requires an even more refined technique or approach than is currently available or applied.

SUMMARY

There is provided a multi-stage nutrigenomic diagnostic test system for screening or testing for food sensitivity or intolerance in animals, in particular companion animals, such as dogs, cats, rabbits, hamsters, and horses.

In particular there is a system for providing staged testing from a first test protocol, being saliva or other mucosal fluid based test, followed by a serum based test protocol and then a genetic DNA/RNA nutrigenomic test protocol. In other cases there is a system for providing staged testing from a first test protocol, being a serum based test protocol and then a DNA/RNA nutrigenomic test protocol. In yet further cases there is a system for providing staged testing from a first test protocol, being a saliva based test, followed by a DNA/RNA nutrigenomic test protocol.

A multi-stage method for diagnosing an immunologic food sensitivity or intolerance in a companion animal. Firstly saliva or other non-serum bodily fluid sample is collected. The screening the saliva or other non-serum bodily fluid sample detects the presence of at least one of IgA or IgM antibody to a particular food ingredient or composition. An immunologic food sensitivity or intolerance based on the presence of the antibody is diagnosed. Secondly a blood sample is collected and serum from the sample is screened to detect the quantitative presence of at least one of an IgA, IgM or IgG antibody or immune complex to a particular food ingredient or composition. An immunologic food sensitivity or intolerance based on the presence of the antibody or immune complex is diagnosed. Thirdly a biologically active nutrient in relation to the animal from a molecular dietary signature is determined. The molecular dietary signature for the animal is a variation of expression of a set of genes, proteins or metabolites which may differ for the genotype of each animal.

Immunglobulins in companion animals differ from those in humans in certain structural and functional aspects in blood, body fluids and tissues. Specifically, cats have significantly more IgA in saliva and serum than dogs or humans, although dogs also have less serum IgA than humans. Levels of IgA and IgM are correlated in dog saliva and tears, but there are conflicting data regarding the correlation between serum and secretary IgA levels in dogs. Further, cats with oral diseases such as gingivitis or stomatitis have increased levels of salivary IgG and IgM but less salivary IgA, whereas serum levels of all three of the immunoglobulins are uniformly increased. Salivary immunoglobulin levels in cats remain relatively constant whereas those of dogs vary from day to day and there may be diurnal variation with higher levels in the afternoon.

Similarly, the salivary and serum IgM levels of dogs and cats are higher in amounts from those of humans.

Saliva can be used as a diagnostic tool to assess the health or disease status of an animal. Saliva is easily collected, stored and shipped, and provides a non-invasive means of multiple or serial sampling for use as a diagnostic tool for a variety of conditions in animals.

The measurement of selected blood (serum) and salivary antibodies is compared in healthy individual animals and in those animals known to have or suspected of having food sensitivities or intolerances. The reliability of saliva testing depends on knowing the correlation or differences between the salivary and blood concentrations, activity, or constituents of a particular substance. The transfer of substances from blood into the saliva or vice versa is dependent on their physiochemical properties. Faster transfer rates of molecules are associated with small molecular weight and great lipid solubility.

A good correlation exists between the saliva/blood ratio of substances and salivary pH. Salivary flow rate and any existing pathophysiology of the oral cavity have also been shown to affect salivary distribution of substances. Saliva content of antigens and antibodies reflects the nutritional and metabolic status of the body, as well as the metabolic, hormonal, biochemical, physiological, immunological or even emotional, status of the individual animal.

Food sensitivity testing for common offending allergens and peptides in dogs or cats is achieved. The sensitivity and testing is for grains most often associated with inflammatory bowel disease ("leaky-gut syndrome, intestinal dysbiosis) or and other symptoms of adverse food reactions—such as, but not limited to wheat and other glutens, corn and soy. These three grain types are among the major constituents (top 5 ingredients) that make up the bulk of standard commercial pre-processed and pre-compounded kibble fed to most dogs or cats. Another common allergen in pet foods or animal food compositions is beef, and the testing and screening is also directed to but not limited to other meats, fish, dairy, eggs, other grains, botanicals, oils from seeds or fish, botanicals, vegetables, or fruit.

The disclosure uses a species-specific test for companion animals such dogs or cats, and other animal species, and the appropriate methods.

This disclosure relates to a diagnostic test system for screening or testing for sensitivity or intolerance to pet food constituents or compositions for a domestic animal, particularly for a dog or cat, and for other species, such as food and fiber animals, and horses.

In particular, the disclosure relates to a diagnostic test system for screening or testing for sensitivity or intolerance of a complete food or food supplements in a dry form, semi-dry form, powdered, or a wet form integrated with functional or nutraceutical compounds from plant or other origins.

The disclosure relates to a diagnostic test system for screening or testing for sensitivity or intolerance to different botanicals or other micronutrients. The activity and the efficacy of the botanicals or other micronutrients depend upon the individual genetic make up of an individual.

The disclosure uses genetic information of DNA polymorphism, the functional genomic profile, and the different response of an individual animal to a biologically active nutrient in order to identify and improve upon or optimize the nutrient composition of the diet for an individual animal.

A unique feature of the disclosure is that the response to a biologically active nutrient ingestion or exposure is a dynamic event since it depends upon the genetic variants of nutritionally inducible genes (polymorphisms, as SNPs) that can lead to a different effect of the biologically active nutrient in individual animals having different genotypes.

Effectively, the genotype of the individual animal is an essential component of this disclosure to permit the identification of the biologically active nutrient for that individual animal.

The assessment of the biologically active nutrient composition of the diet arises from using reference data relating to healthy animals with different genotypes, plus target data relating to animals affected with different physiological or pathophysiological states [termed "unhealthy animals"] and having different genotypes, and nutritional data relating to the different effects of nutritional compounds in healthy and unhealthy animals or groups of animals with different genotypes.

Additional and further objects, features, and advantages of the present disclosure will be readily apparent to those skilled in the art.

DETAILED DESCRIPTION OF THE DISCLOSURE

Figure 1:
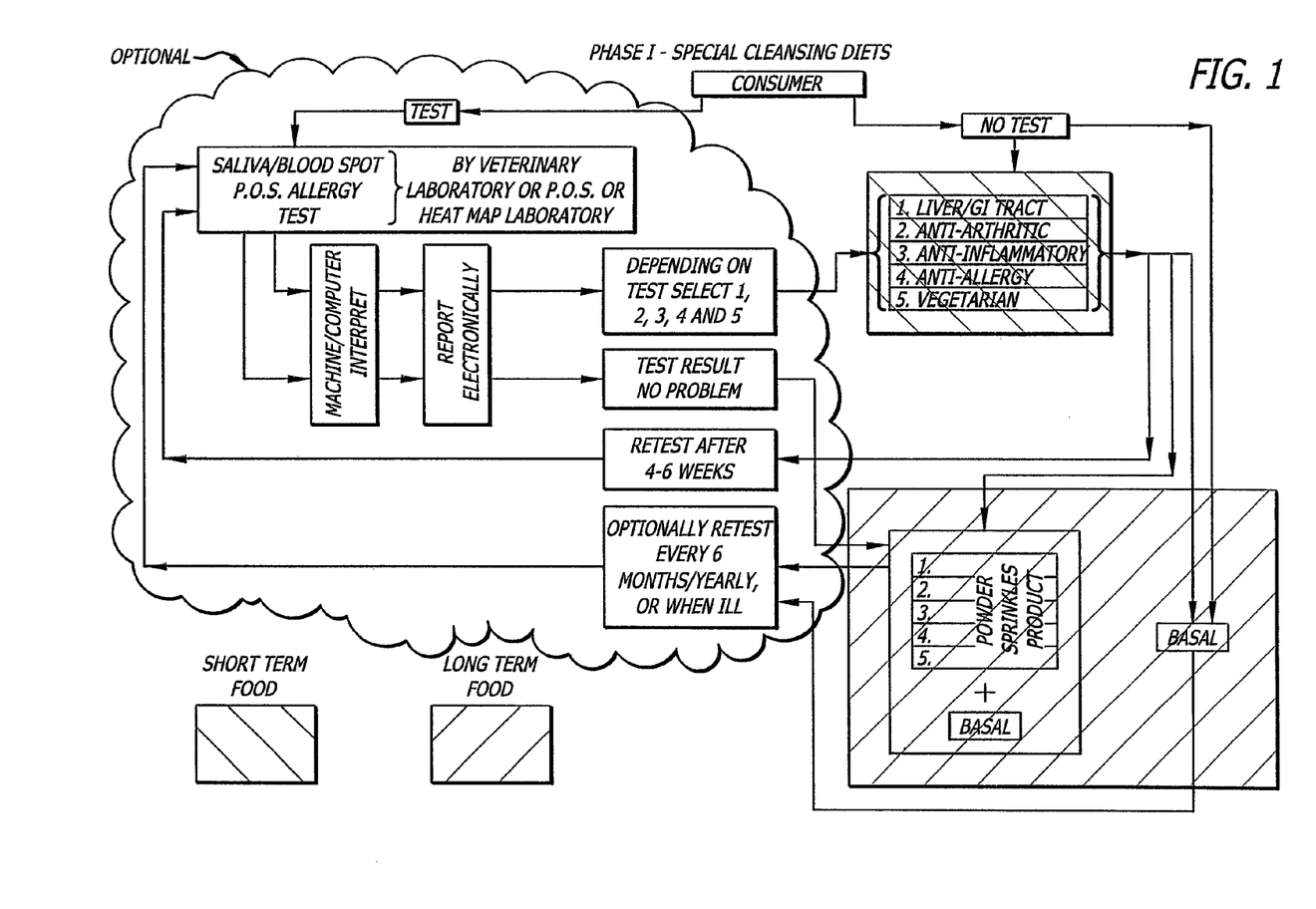
FIG. 1 is a schematic illustrating the determining and prescribing of a Phase I special cleansing diet food regime in conjunction with the food sensitivity and intolerance testing. The testing is conducted in a veterinary laboratory or by Point of Service ("P-O-S") device. The diets here are for liver/GI tract, anti-arthritic, anti-inflammatory, anti-anti-allergy and vegetarian. There may be less or more of these diets. The testing is interpreted by machine, reader or computer and then reported electronically.
Figure 2:
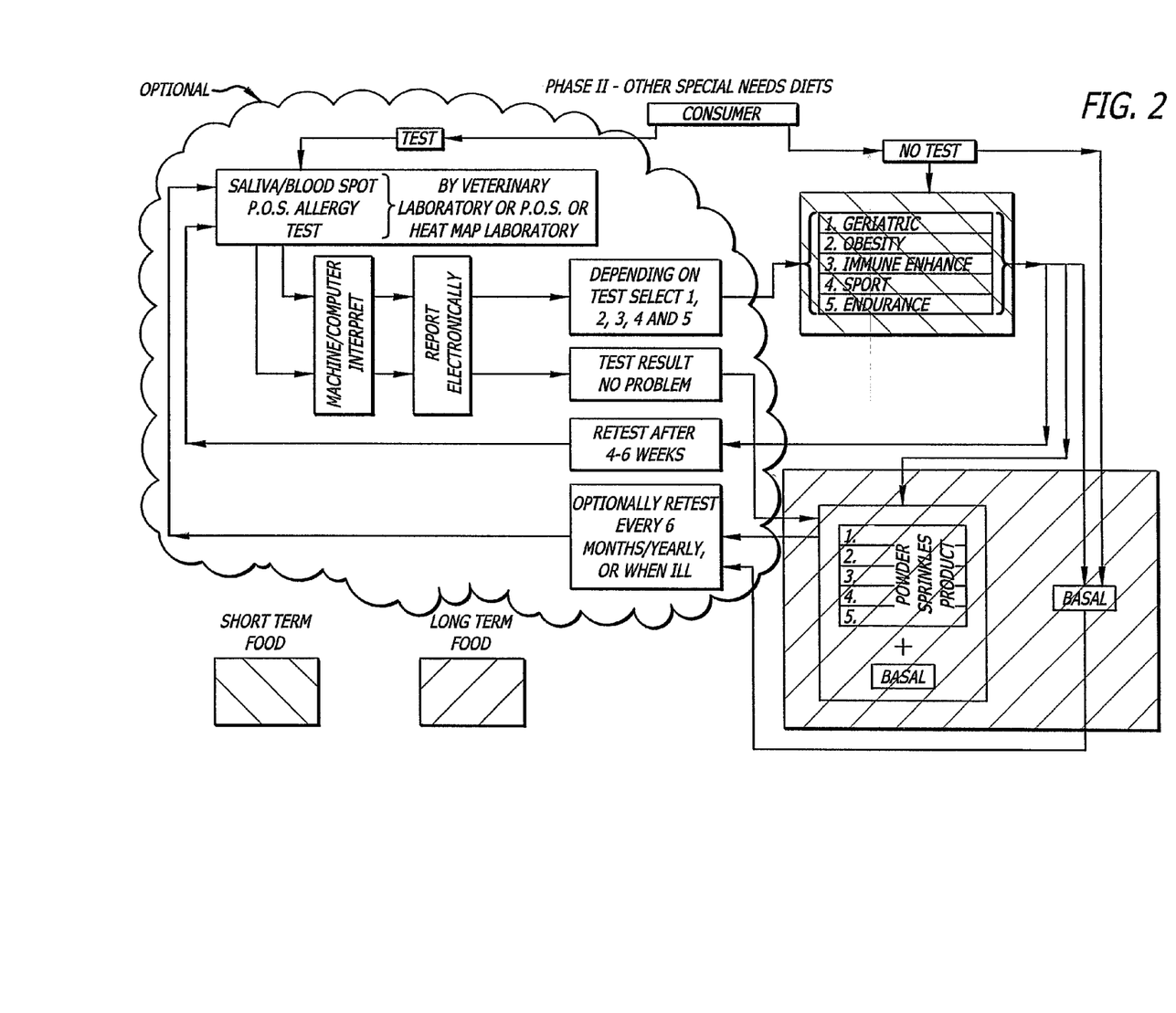
FIG. 2 is a schematic illustrating the determining and prescribing of a Phase II "Other Special Needs Diets" food regime in conjunction with the food sensitivity and intolerance testing. The testing is conducted in a veterinary laboratory or by P-O-S device. The diets here are for geriatric, obesity, immune enhancement, sport or endurance purposes. There may be less or more of these diets. The testing is interpreted by machine, reader or computer and then reported electronically.

There is a need to facilitate the choice of a pet food to suit selected animals so that there is compatibility between the pre-prepared balanced and integrated food composition or mixture of macro- and micro-ingredients and the physiological, metabolic, biochemical or genetic makeup of the pet or companion animal. Most companion animals are fed commercially pre-mixed, pre-compounded, or constituted macro- and micro-ingredients such that there is a single integrated food with such pre-mixed and pre-integrated ingredients. This is usually stated to be the complete or main stay or basic food or diet for the companion animal. Thus, normally such companion animals receive as their regular so-called healthy and nutritious diet one or more regular pre-packaged mixtures of ingredients in commercially prepared foods.

This is largely different to human diets which are generally not pre-packaged as a complete single food with the necessary macro- and micro-ingredients for a complete and healthy diet. Instead the human diet is typically formed with variety and is selected from multiple ingredients which are assembled by choice or purpose, and specifically prepared and cooked on a custom basis according to the individual choice and preference of a human, and specifically for different meals or meal combinations.

The food ingredient or ingredients for which the method of the disclosure is performed is contained in a composition being at least one of a pre-processed food composition, balanced diet or recipe composition. The testing is performed to identify which ingredient(s) from that group of pre-packaged and pre-mixed companion animal foods create sensitivity or intolerance. This can be a moist or semi-moist food, dry kibble or an extruded cereal product. The majority of companion animals or pets in developed countries are fed by this commercially generally available off the shelf pre-prepared pet food mixtures. Sensitivities or intolerances to these foods often arise, but there is no simple manner of determining which ingredient(s) in those foods causes the sensitivity or intolerance.

The disclosure relates to multistage or staged testing for food sensitivity from different test protocols. There is a saliva based test protocol, followed by a serum based test protocol and then a DNA/RNA nutrigenomic test protocol. In other cases there is staged testing from a first test protocol, being a serum based test protocol and then a DNA/RNA nutrigenomic test protocol. There is also a system for providing staged testing from a first test protocol, being a saliva based test, followed by a DNA/RNA nutrigenomic test protocol.

In many cases there are a high proportion of animals requiring the saliva testing, and the testing is performed frequently during a life span of an animal. Such testing can often be performed by a lay person such as the owner of the animal. The serum stage requires the taking of blood from the animal, usually by a veterinarian or veterinary technician. This testing will be required less frequently during the lifetime of the animal. The most sophisticated testing, the nutrigenomic heat map testing, will be required less frequently by a smaller percentage of the overall population of animals. This required a blood sample from the animal and processing in a high throughput ("HTP") DNA/RNA measuring system in a laboratory.

The present disclosure permits for integrated single stage testing steps for multiple antigens following the intake of a pet or companion animal multi-ingredient food product. The single stage bodily fluid test, tests for multiple antigens in the food product.

In one form of the disclosure, the companion animal is tested by giving such a food being a pre-prepared integrated pre-mixture of ingredients containing the multiple macro- and micro-ingredients for the animal. Then the animal is subjected to at least one of the testing and diagnostic procedures. In this manner it is possible to determine which ingredient(s) in a pre-processed food composition, balanced diet or recipe induces a possible sensitivity or intolerance issue. An assessment is made as to whether different pre-processed or pre-packaged food compositions, balanced diets or recipes are available to offer more appropriate, compatible food(s). In some cases it may necessary to determine whether a special diet needs to be formulated without the offending ingredient or ingredients.

Food sensitivity or intolerance has an immunological basis. It is not possible to distinguish a food which elicits an immunological response from the related intestinal disease or disorder that reflects the body's reaction to the food ingredient or ingredients. The description provided is primarily related to detecting immunologic food sensitivities or intolerances in animals.

A primary example of a food sensitivity or intolerance is sensitivity to wheat or other gluten foods, for example barley, rice, millet, and oats. In the Irish Setter breed, for example, wheat-sensitive enteropathy is a heritable condition. Immunological reactions to gluten foods causes atrophy of the intestinal villi and inflammation of the small intestine, which, in turn, results in diarrhea and weight loss from malabsorption of fluid, electrolytes, and dietary nutrients. Even though chronic or intermittent diarrhea and intermittent vomiting are the most common symptoms of this food sensitivity, there have been few studies of the prevalence of this condition in animals being presented to veterinarians with chronic diarrhea or vomiting or other common gastrointestinal symptoms. Furthermore, beyond costly measurements of serum IgE-mediated antibodies, there are no adequate methods in veterinary medicine to diagnose or noninvasively test for immunologic food sensitivities or intolerance. This frequently results in either no diagnosis or the missed diagnosis of an immunologic food sensitivity or intolerance.

Despite this situation, many animals with gluten or other food sensitivity or intolerance do not have diarrhea or weight loss, but instead have other signs and symptoms such as vague abdominal pain, nausea, abdominal bloating, flatulence, chronic fatigue, constipation, poor growth and maturity, iron deficiency anemia, osteoporosis, seizures or other neurologic disorders, or even just elevated serum liver enzyme levels. Some animals may be asymptomatic.

Furthermore, animals with gluten or other food sensitivity or intolerance may not have fully developed intestinal lesions. Therefore, the food sensitivity or intolerance of these animals may not be properly diagnosed using known testing methods, such as endoscopic intestinal biopsy and blood or serum testing. Additionally, these animals may present with other immunologic diseases such as the autoimmune diseases of skin, liver, joints, kidneys, pancreas, and thyroid gland, or microscopic colitis.

One form of the disclosure relates to a method for diagnosing a food sensitivity or intolerance in a companion animal comprising the steps of firstly collecting a saliva sample; screening the saliva or blood spot sample to detect the qualitative or semi-quantitative or quantitative presence of at least one of an IgA, IgM or IgG antibody to a particular food ingredient or composition. Diagnosing a food sensitivity or intolerance based on the presence of the antibody, is then effected.

A second form of the disclosure involves collecting a blood sample; and preparing serum from the sample; screening the serum sample to detect the qualitative or semi-quantitative or quantitative presence of at least one of an IgA, IgM or IgG antibody or immune complex to a particular food ingredient or composition. Diagnosing a food sensitivity or intolerance based on the presence of the antibody or immune complex is affected.

In some cases the first and second steps are selectively divided into two stages, the first stage being a qualitative step to determine the food sensitivity, followed by a semi-quantitative or quantitative step.

This disclosure is based on an Enzyme-Linked Immunosorbant Assay (ELISA), or other immunoassay platforms such as but not limited to lateral flow, or latex or bead agglutination, which measures the presence of at least one of IgA, IgM or IgG antibodies or immune complexes against a wide variety of foods or food supplements or food additives in an animal's serum, as well as at least one of IgA, IgM or IgG antibodies in an animal's saliva or blood spot or other bodily matter.

The current disclosure measures at least one of, and preferably more than one of serum IgA, IgM or IgG or immune complexes that may be mediated by complement. Also, at least one of, and preferably more than one of salivary or blood spot or other bodily fluid IgA, IgM or IgG is measured.

The amount of these antibodies in serum and saliva or blood spot or other bodily matter of healthy individual animals is compared to that in serum and saliva or blood spot or other bodily matter of animals with clinically expressed or suspected pre-clinical or latent food sensitivity or intolerance.

One method associated with the disclosure is for diagnosing a food sensitivity or intolerance in companion animals which comprises the steps of: collecting a blood sample; preparing serum from the sample; screening the serum sample to detect the presence of at least one of, and preferably more than one of an IgA or IgG antibody or immune complex to a particular food ingredient or composition. Thereafter there is a diagnosis of a food sensitivity or intolerance based on the presence of the antibody or immune complex. Another method associated with the disclosure is for diagnosing an food sensitivity or intolerance in companion animals comprising the steps of: collecting a saliva or blood spot sample; screening the saliva or blood spot sample to detect the presence of at least one of, and preferably more than one of an IgA or IgM or IgG antibody or immune complex or immune complex with complement to a particular food ingredient or composition. Thereafter there is a diagnosis of a food sensitivity or intolerance based on the presence of the antibody or immune complex or immune complex with complement.

The method for diagnosing a food sensitivity or intolerance in a companion animal can comprise the steps of obtaining a sample of a serum, non-serum biological fluid, selectively saliva or blood spot or other non-serum bodily fluid or matter. The sample is screened to detect the presence of at least one of an IgA, IgM or IgG antibody or immune complex or immune complex with complement to a particular food ingredient or composition. A food sensitivity or intolerance is diagnosed based on the presence of the antibody or immune complex or immune complex with complement.

Where the sample is saliva or blood spot or other bodily fluid or matter, a testing portion from the saliva or blood spot or other bodily fluid or matter is collected and the testing portion is the sample in the screening step. The sample is about 1-5 milliliters or about 1-15 grams.

The screening step utilizes an immunoassay, selectively an enzyme-linked immunosorbant assay (ELISA) testing system to detect the presence of an antibody immune complex or immune complex with complement to a particular food ingredient or composition of food ingredients.

Another method associated with the disclosure is for diagnosing a food sensitivity or intolerance in companion animals comprising the steps of collecting a saliva or blood spot sample; screening the saliva or blood spot sample to detect the presence of at least one of, and preferably more than one of an IgA or IgM or IgG antibody to a particular food ingredient or composition.

Thereafter there is a diagnosis of a food sensitivity or intolerance based on the presence of the antibody, and collecting a blood sample; preparing serum from the sample; screening the serum sample to detect the presence of at least one of, and preferably more than one of an IgA, IgM or IgG antibody or immune complex to a particular food ingredient or composition.

Thereafter there is a diagnosis of a food sensitivity or intolerance based on the presence of the antibody or immune complex.

The food sensitivity is at least one of wheat or other gluten sensitivity or intolerance, corn or soy, beef or other meat or fish protein sensitivity or intolerance or dairy, eggs, other grains, botanicals, oils from seeds or fish, vegetables, or fruit sensitivity or intolerance.

The food ingredient for which sensitivity or intolerance is being tested is contained in at least one mixed ingredient food having multiple ingredients in varying amounts of a premixed food composition, balanced diet or recipe.

The companion animal is tested by giving such a mixed food to the animal. The animal is then tested and a sensitivity or intolerance diagnosis is made by determining the reaction of the animal to different foods and specific selected ingredients. In this manner it is possible to determine whether there is and if so which ingredient in a preprocessed food composition, balanced diet or recipe is a potential or real sensitivity or intolerance problem for a specifically tested animal. An assessment is made as to whether it is possible to use a different preprocessed mixed food composition, balanced diet or recipe, or whether a special diet needs to be formulated without the offending ingredient or ingredients.

The test methodology of the present disclosure differs significantly from all others available for use in animals. It is highly reproducible and clinically relevant. In serum, the food antigen or peptide being tested and at least one of, and preferably more than one of any specific IgA or IgG antibody in serum, bind to each other and then fix complement. In saliva or blood spot or other bodily fluid, the food antigen or peptide being tested reacts directly with the IgA or IgM antibody in the test animal's saliva or blood spot or other bodily fluid. Common animal food antigens (such as wheat or other glutens, corn and soy, beef or other meats, fish or other foods and botanicals) are bound to wells in a 96-well standard ELISA microtiter plate so that they are non-reactive until an animal's serum or saliva or other bodily fluid is added. Specific binding of IgA or IgG antibody or immune complexes in serum or IgA or IgM antibody in saliva or blood spot or other bodily fluid to specific food ingredients is identified by finding increased levels of one or more of these antibodies in test, unhealthy or suspect individuals in comparison to healthy control animals.

In another embodiment, the salivary or blood spot or other bodily fluid testing uses a quantitative or semi-quantitative point-of-service (P-O-S) test kit system, whereby the animal owner or veterinarian or other designated tester collects the saliva or other bodily fluid from individual healthy animals or unhealthy or suspect animal patients. The requisite biological sampling swabs or straws are provided in the P-O-S test kit; the collected saliva or other bodily fluid is added to the test kit chamber, and the chamber is sealed and submitted to the testing laboratory for quantitative analysis. This is a single stage test for multiple antigens.

In another embodiment, the salivary or other bodily fluid testing uses a quantitative point-of-service (P-O-S) test kit system, in which the requisite salivary or other bodily fluid biological sampling swabs or absorbent paper or straws are provided. The collected saliva or other bodily fluid is added to a special well in the test kit chamber, which is then allowed to react by capillary attraction with a series of microchannels containing various food antigens or peptides of interest within the chamber's lateral flow device. Once the reaction is completed, the chamber is sealed and submitted to the testing laboratory for semi quantitative or quantitative analysis. This is a single stage test for multiple antigens.

In a further embodiment, the salivary or blood spot or other bodily fluid testing uses a quantitative r semi-quantitative point-of-service (P-O-S) test kit system, in which the requisite salivary or blood spot or other bodily fluid biological sampling swabs or absorbent paper or straws are provided. The collected saliva or blood spot or other bodily fluid is added to a special well in the test kit chamber or dipped into a test strip, which is then allowed to react by capillary attraction across a reagent strip containing various food antigens or peptides of interest within the strip, much like the existing urine dip-stick technology strips, routinely used in human and veterinary medicine. Once the reaction is completed, qualitative reactions are read on a color-grading scale provided with the kit. These reactions can range from negative or little to no color reaction to a highly reactive intense color development. This is a single stage test for multiple antigens.

Positive qualitative reactions seen with the P-O-S test kit can help to identify the major food reacting antigens or peptides in an animal's saliva or blood spot or other bodily fluid, but should be confirmed by one or more of the semi quantitative or quantitative serum or saliva or blood spot or other bodily fluid tests described in this disclosure. This is a single stage test for multiple antigens.

For semi-quantitative or quantitative testing, an animal's serum or blood spot or saliva or other bodily fluid is added to the ELISA microtiter plate or other immunoassay platforms such as but not limited to lateral flow, or latex or bead agglutination, which measures the presence of IgA, IgM or IgG or immune complexes against a wide variety of foods or food supplements or food additives in an animal's serum, as well as in an animal's saliva or blood spot or other bodily fluid and any specific antibodies present directed against IgA, IgM or IgG antibodies or immune complexes (serum) or IgA, IgM or IgM antibodies (saliva) or blood spot or other bodily fluid are then bound to their respective food antigens or peptides. The plate is washed and an enzyme conjugate is added that recognizes the bound antibodies of IgA, IgM or IgG or immune complexes in serum, and IgA or IgM in saliva or blood spot or other bodily fluid. After incubation and washing, substrate is added to visualize the bound antibodies of IgA, IgM or IgG or immune complexes in serum, and IgA or IgM or IgG in saliva or blood spot or other bodily fluid. The amount of the optical density recorded is proportional to the amount of bound antibody to IgA, IgM or IgG or immune complexes in serum, and IgA or IgM or IgG in saliva or other bodily fluid. A report depicting these reactions is plotted on a simple bar graph or by other means. Results show with a high degree of accuracy if an animal patient has a positive or negative reaction against a particular food ingredient.

Food Sensitivity or Intolerance Reactions

Research to date has shown that serum IgA or IgG alone, or with complement, constitute the main immunologically reactive pathways of foods and food supplements. In saliva or other mucosal secretions or other bodily fluids such as tears or milk, the main immunologic reactants are IgA or IgM. These reactive immune responses are characterized classically as Types I, II, III, and IV hypersensitivities.

Type I immune reactive responses are mediated by IgE antibody, and are commonly called an immediate hypersensitivity. This allergic reaction occurs within two hours of allergen exposure or ingestion.

Type II immune reactive responses are mediated by IgG or IgM antibodies and are commonly called delayed hypersensitivity. The allergic reaction occurs from two hours to several days after allergen exposure.

Type III hypersensitivity responses form an immune complex that is also a delayed hypersensitivity, because the allergic reaction occurs days to weeks post allergen exposure or ingestion. Type III reactions develop when immune complexes, typically of the IgG class form in such large quantities that they cannot be cleared adequately by the reticuloendothelial system. Allergen exposure results in production of IgG, which then binds to the allergen, forming immune complexes in the blood. These immune complexes in turn activate complement, resulting in the covalent binding of complement component C3b to the IgG, thereby forming immune complex-C3b. The immune complexes so formed are deposited at various sites throughout the body, and damage ensues when they are deposited and further activate complement, producing and releasing inflammatory cytokines. Release of cytokines causes leukocytes to release proteases, mast cells and vasoactive amines that damage blood vessels and escalate the inflammatory process.

Type IV immune reactive responses represent the cell-mediated form of delayed hypersensitivity. The allergic reaction occurs days to weeks after allergen exposure. The most serious type of delayed hypersensitivity is a granulomatous tissue rejection, which occurs when macrophages ingest but cannot degrade an offending allergen, thereby resulting in persistent stimulation of tissue macrophages. Stimulated macrophages elaborate cytokines that cause the macrophages and other cell types to concentrate around and in the area of tissue injury. T-lymphocytes are then stimulated in turn by cytokines, which activate complement and induce immune-complex formation.

Measuring IgE remains the standard for determining the presence of inhalant allergies (atopy), but this method usually fails or is too costly when diagnosing food sensitivity or intolerance as related to chronic diseases.

Delayed food-related sensitivities begin in the gastro-intestinal tract when the intestinal lining becomes hyperpermeable. This problem is known as "leaky gut syndrome" or intestinal dysbiosis, and is defined as an increase in permeability of the intestinal mucosa to partially digested protein macromolecules, micromolecules, antigens and toxins. The immunological reaction to these proteins or other molecules in the liver initiates and perpetuates chronic food sensitivity or intolerance. When the gut is unhealthy, the rest of the body is unhealthy. The disease process that ensues is typically chronic or intermittent and often involves the gut and skin, as well as internal organs such as the liver. Gastro-intestinal tract function is disrupted when the lining of the gut is inflamed or damaged. With a leaky gut, large food antigens can be absorbed into the body. The body's defense systems then attack this antigen or antigens and the result is the production of antibodies against what was once a harmless, innocuous food ingredient. These IgA or IgG antibodies and immune complexes are formed in the bloodstream and circulate throughout the body where they can damage other tissues along the way. In saliva or other bodily fluid, these reactants are typically IgA or IgM.

Immune Complex

Immune complexes containing large food antigens enter the blood from the gastro-intestinal tract then travel through the liver where most immune complexes are removed. However, if circulating immune complexes pass the liver filtering system, they may cause injury to many body tissues. Malabsorption of food particles from the gastro-intestinal tract can also travel by lymphatic drainage to the body. The lymph channels in the gut wall converge at the thoracic duct which drains its contents into the large thoracic veins. This combination of antibody with complement in the blood stream becomes a circulating immune complex. Immune complexes subsequently attach to receptors on red and white blood cells and then these altered cells are cleared by the body's liver or spleen (reticuloendothelial system).

Any circulating immune complexes that are not removed by the reticuloendothelian system of the liver (or spleen) can activate the complement cascade. Individuals with more immune complexes on their red blood cells are the ones that suffer from chronic food sensitivities or intolerances.

Circulating immune complexes also can damage the integrity of blood vessel capillaries which in turn can trigger inflammatory events.

Diagnosing Immunologic Food Sensitivity or Intolerance by Blood or Saliva Testing Samples for Antibodies or Immune Complexes A blood serum or saliva or blood spot or other bodily fluid sample from the animal patient is shipped to the laboratory for testing. Although this is one method for collecting a sample from a patient, it is recognized that other methods of obtaining a sample may be used within the scope of the disclosure. Such methods include taking the patient physically to a veterinary clinic or laboratory to collect a blood sample to prepare its serum, or a saliva or blood spot or other bodily fluid sample, or, could include a P-O-S qualitative saliva or blood spot or other bodily fluid screening test performed by the pet owner or veterinarian or other person.

Once collected at or received by the lab, the blood serum or blood spot or saliva or other bodily fluid sample is then screened using the ELISA method or other immunoassay platforms such as but not limited to lateral flow, or latex or bead agglutination, which measures the presence of selected IgA or IgG antibodies or immune complexes against a wide variety of foods or food supplements or food additives in an animal's serum, as well as IgA or IgM antibodies in an animal's saliva or blood spot or other bodily fluid. The detection of a particular antibody in the patient serum or saliva or blood spot or other bodily fluid at a level higher than that seen in healthy animal patients then forms the basis for a diagnosis of the food sensitivity or intolerance associated with that antibody.

In one form there is provided a diagnostic test system for screening or testing for food sensitivity or intolerance in animals of the food composition which can comprise at least several active components of wheat or other gluten foods, corn, soy, beef or but not limited to other meats, fish, dairy, eggs, other grains, botanicals, oils from seeds or fish, botanicals, vegetables, nuts, or fruit sensitivity or intolerance.

In another form there is provided a diagnostic test system for screening or testing for food sensitivity or intolerance in animals of other constituents including a group of and at least macro- and micro-components such as vitamins, amino acids, and one or more plant, part of plants and plant extract(s) having functional and nutraceutical properties.

There is also provided a diagnostic test system for screening or testing for food sensitivity or intolerance in animals of the activity of one or more protein compounds, depending upon the food ingredients, the physiology of the animal's digestive tracts and the individual genetic make up of the animal.

There is provided a diagnostic test system for screening or testing for food sensitivity or intolerance in animals that individually respond with an immune reactive response to functional, nutraceutical or therapeutic compounds, and which depends upon the genetic make up of the animal, which differs from the ability to adapt to the environment and to interact with nutrients.

There is provided a diagnostic test system for screening or testing for food sensitivity or intolerance in animals that the activity and the efficacy of functional, nutraceutical and therapeutic compounds of plant or other origin depends upon their molecular dietary signature, which is related to the individual genetic make up, according to the concept of nutrigenomics.

The immune reactive response of a pet animal is dependent upon its genetic make up that is the coordinated and integrated relationship among genes which can be differently regulated from botanicals or other compounds, according to the individual genotype; the gene(s) act downwards (down-regulated) and upwards (up-regulated) in the regulation of molecular, cellular and biological pathways.

There is provided a diagnostic test system for screening or testing for food sensitivity or intolerance in animals that wherein the adverse immunologic reaction effect of the ingredients can also vary according to the genotype of pet animals, and the variability of individual animals.

The compounds and food ingredients can induce a variable reactive immune response to the physiological or pathological response of an individual pet animal. This can be expressed by what is termed "leaky gut syndrome" or intestinal dysbiosis. Furthermore, the gut dysbiosis in turn can lead to damage or malfunction of other body tissues, especially the skin. This is termed the "gut-skin connection."

The term "pet" means a domestic dog, cat or horse. The term "pet food composition" means a food composition or feed ingredient that is intended for ingestion by the pet. Pet food compositions may include, without limitation, nutritionally balanced compositions suitable for daily feed, as well as supplements which may or may not be nutritionally balanced.

The pet food compositions that induce adverse immune reactions or food sensitivities may be prepared by any of a variety of processes. The components may be obtained from plant or vertebrate animal matter, or otherwise provided, and then subjected to pet food processing, as meal, pellet, cold extrusion, heat extrusion autoclaved tins and pouches.

There is provided a diagnostic test system for screening or testing for food sensitivity or intolerance in animals, of the offending food ingredients being in preprocessed or premixed pet food meals, biscuits, snacks, treats, sprinkles, candies and other form of foods.

The ELISA testing system, or other immunoassay platforms such as but not limited to lateral flow, or latex or bead agglutination, are well known in the art. These assays measure the presence of selected IgA or IgG antibodies or immune complexes against a wide variety of foods or food supplements or food additives in an animal's serum, as well as IgA or IgM antibodies in an animal's saliva or blood spot or other bodily fluid. The presence of these IgA or IgG antibodies or immune complexes in a patient's serum is tested against one or more of a selected panel or group of food antigens or ingredients. The presence of IgA or IgM antibodies in saliva or blood spot or other bodily fluid is also tested against one or more of a selected panel or group of food antigens or ingredients. If the results show an increased level of any of these selected antibodies to food antigens or ingredients in the serum or saliva or blood spot or other bodily fluid of a patient in comparison to those levels of the same selected antibodies in healthy animals, the findings indicate that the animal patient does in fact have a particular immunologic food sensitivity or sensitivities or intolerance. The animal patient should then be treated accordingly by removing the triggering substance or substances from the diet or by other methods known in the art.

Although specific parameters and equipment have been discussed in this aspect of the disclosure, it is understood that the parameters may differ and that different equipment may be used to carry out the disclosed methodologies without deviating from the scope of the disclosure.

This blood serum or saliva or blood spot or other bodily fluid testing method may be combined with one or more other immunologic food sensitivity or intolerance diagnostic indicators previously described according to other established methods in order to further enhance the sensitivity and accuracy of immunologic food sensitivity or intolerance diagnosis.

Secretory IgA serves as a mucosal barrier to certain macromolecules, bacteria, and viruses. When these molecules or organisms interact with secretory IgA and the mucosa, their entrance and exposure to the gut-associated lymphoid tissue (GALT) is blocked. This blockage permits the host to shield efficiently the systemic immune response, local immune response, or both, from onslaught of foreign molecules.

Secretory IgA therefore has anti-bacterial, anti-fungal, and anti-viral activities, and plays an important role in protection of mucosal surfaces from adherence of microorganisms.

Another important role of secretory IgA is in prevention of the diffusion of food antigens into mucous membranes.

Despite the enteric route of exposure to food antigens and peptides, food-specific antibodies are typically measured only in blood, and not in saliva or other bodily fluid.

The disclosure includes using a bodily fluid of a companion animal such as saliva to determine food sensitivity of that animal. Saliva is an accessible fluid, easy to collect, and demonstrates representative responses in secretions after enteric or intragastric antigenic challenge.

The disclosure includes measuring at least one of, and preferably more than one of salivary or other bodily fluid IgA or IgM against different food antigens and peptides for use in determining food allergy and food intolerance in companion animals.

A method for determining the presence of food allergy or food intolerance in a companion animal such as a dog or cat or horse includes (a) determining at least one of, and preferably more than one of the level of salivary or other mucosal or other bodily fluid IgA or IgM antibody or antibodies against a dietary antigen or peptide present in a food in a saliva or other mucosal or other bodily fluid sample from the animal; and (b) comparing the level determined in step (a) with normal levels of the antibody or antibodies in the mucosal or other bodily fluid sample.

The possible outcomes for the comparison include (i) lower than normal levels or about normal levels of dietary antigen antibodies indicate optimal conditions; and (ii) higher than normal levels of dietary antigen antibodies indicate a food allergy or food intolerance.

There is a also a method for determining a type of antibody in a presence of food allergy or food intolerance to a food in an animal, comprising (a) determining a level of antibodies against a dietary antigen or peptide present in the food in a first saliva or other mucosal or other bodily fluid sample from the animal patient; (b) determining a level of antibody or antibodies against cross-reactive tissue antigen or antigens or peptides present in a second salivary or other mucosal or other bodily fluid sample from the animal patient, wherein the first and second samples are the same or different; and (c) comparing the level of antibody or antibodies determined in steps a) and b) with normal levels of the antibody or antibodies found in healthy animals.

The possible outcomes for the comparison include (i) essentially normal levels of antibody or antibodies against the dietary antigen or peptide and normal levels of antibody or antibodies against cross-reactive tissue antigen or peptide indicate optimal conditions; (ii) higher than normal levels of antibody or antibodies against the dietary antigen and essentially normal levels of antibody or antibodies against cross-reactive tissue antigen or peptide indicate food allergy and intolerance without cross-reacting to tissue antigen or peptide; (iii) essentially normal levels of antibody or antibodies against the dietary antigen or peptide and higher than normal levels of antibody or antibodies against cross-reactive tissue antigen or peptide indicate an autoimmune reaction not related to the dietary antigen or peptide; and (iv) higher than normal levels of antibody or antibodies against the dietary antigen or peptide and higher than normal levels of antibody or antibodies against cross-reactive tissue antigen or peptide indicate a presence of food allergy and intolerance resulting in an autoimmune reaction.

A test informs a pet owner of clinical conditions of their pet who may suffer from food sensitivities, allergies or food intolerance. The test uses a method that measures antibody titers to dietary antigens. The test method measures the antibodies' ability to bind to a recombinant antigen, synthetic peptide, a peptide prepared by enzymatic digestion corresponding to the dietary antigen, or different cross-reactive tissue antigen or antigens.

There is an immunoassay for detecting food allergies and food intolerance in a patient using mucosal or other bodily fluid secretions. Mucosal secretions are secretions of a mucosa, such as saliva.

Forms of biological fluid, other than saliva, for instance, blood, feces, urine, tears, or milk or other mucosal secretions can be used.

There is a method for detecting food allergies and food intolerance in an animal. The method includes (a) determining a level of antibody or antibodies against a dietary antigen or peptide in the food in a salivary or other mucosal or other bodily fluid sample from a patient; and (b) comparing the level determined in step (a) with normal levels of the antibody or antibodies in the salivary or other mucosal or other bodily fluid sample.

The possible outcomes for the comparison include (i) lower than normal or essentially normal levels of antibody or antibodies to dietary antigen or peptide indicate optimal conditions; and (ii) higher than normal levels of antibody or antibodies to dietary antigen or peptide indicate a food allergy or food intolerance.

The detection of antibodies can be performed with an immunoassay. Immunoassays include, but are not limited to, ELISA test, RIA test, latex agglutination, beads assay, and proteomic assays. A preferable immunoassay is the ELISA test. Other immunoassays can be used and the choice of immunoassay can be determined by one of ordinary skill in the art.

A normal reading is derived from a baseline measurement taken from antibody measurements for individuals without symptoms relating to food allergies or food intolerance. A baseline measurement for the test is obtained by observing the antibody measurements for individuals without symptoms relating to food allergies or food intolerance. For example, most readings for antibody measurements from an individual without symptoms relating to food allergies or food intolerance are below a certain reading. Preferably, about 50-100% of the readings from an animal without symptoms relating to food allergies or food intolerance are below the certain reading, more preferably about 60-100%, 70-100%, or 80-100% of the readings, even more preferably about 90-100% of the readings. If an animal exhibits antibody measurement two standard deviations above the baseline, the above-normal antibody measurement indicates the presence of food allergy or food intolerance.

Additionally, antibodies against cross-reactive tissue antigen or antigens may be tested. Cross-reactive tissue antigen or antigens include, but are not limited to, lectins, lectins receptors, tropomyosin, smooth muscle, epithelial cell antigens, enzymes, cytochrome P-450 enzymes, and transglutaminase. Ingested dietary antigens or peptides may induce antibodies that react with the specific dietary antigen and another antigen, such as a cross-reactive tissue antigen. If antibodies against cross-reactive tissue antigens are tested in addition to the dietary antigens, then the antibodies can be determined to be protective or pathogenic.

Essentially normal levels of antibodies against the dietary antigen or peptide and normal levels of antibodies against cross-reactive tissue antigen or antigens indicate optimal conditions. Higher than normal levels of antibodies against the dietary antigen or peptide and essentially normal levels of antibodies against cross-reactive tissue antigen or antigens indicate food allergy and intolerance without cross-reacting to tissue antigen or antigens. Essentially normal levels of antibodies against the dietary antigen or peptide and higher than normal levels of antibody or antibodies against cross-reactive tissue antigen or antigens indicate an autoimmune reaction not related to the dietary antigen or antigens. Higher than normal levels of antibodies against the dietary antigen or peptide and higher than normal levels of antibodies against cross-reactive tissue antigen or antigens indicate a presence of food allergy and intolerance resulting in an autoimmune reaction.

There can be an apparatus and method for conducting a variety of assays for the determination of analytes in samples. There can be a single-use device designed to be adaptable to a variety of real-time assay protocols, preferably assays for the determination of analytes in biological samples using immunosensors or other ligand/ligand receptor-based biosensor embodiments.

There can be a metered portion of a sample, for precise and flexible control of the movement of a sample or second fluid within the device. The device and method is for rapid in situ determinations of one or more analytes, and single-use methodology that minimizes the risk of contamination of both operator and the animal. As such there is a point-of-service (P-O-S) clinical diagnostic use.

A multitude of laboratory tests for analytes of interest are performed on biological samples for diagnosis, screening, disease staging, forensic analysis, pregnancy testing, drug testing, and other reasons. While a few qualitative tests, such as pregnancy tests, have been reduced to simple kits for home use, the majority of quantitative tests still require the expertise of trained technicians in a laboratory setting using sophisticated instruments.

Optical means for detecting the binding of an analyte to a receptor is employed, or alternatively there can be electrochemical detection, in which binding of an analyte directly or indirectly causes a change in the activity of an electroactive species adjacent to an electrode, has also been applied to immunoassay.

Therefore, there exists within the field of analyte sensing, and in particular for applications in which analytes must be determined within biological samples such as blood, a need for apparatus that can rapidly and simply determine analytes at the P-O-S, and can be performed by less highly trained staff than is possible for conventional laboratory-based testing. It would be of benefit in the diagnosis and treatment of critical veterinary conditions for the veterinarian or veterinary technician to be able to obtain clinical test results without delay. The apparatus should be adaptable to determination of a range of analytes and capable of single-use so that there can be disposal of the sample after testing.

A device according to the present disclosure has the advantage that the sample and a second fluid can contact the sensor array at different times during an assay sequence. The sample and second fluid may also be independently formed with other reagents or compounds present initially as dry coatings within the respective conduits. Controlled motion of the liquids within the device further permits more than one substance to be added into each liquid whenever the sample or fluid is moved to a new region of the conduit.

In operation, an amount of a preferably biological sample is placed into the sample chamber of the device. The device can have reading zones or the device can be placed into a reading apparatus. A metered portion of the sample can be amended with at least one antibody-enzyme conjugate, and is then contacted with the immunosensor. A second fluid, which contains an inactive substrate for the enzyme, is used to rinse the immunosensor substantially free of unbound antibody-enzyme conjugate, and the response of the immunosensor is recorded and analyzed for the presence, or amount of, analyte of interest. The device may contain a plurality of immunosensors and reagents.

After the reading, the operator removes and discards the device. The reader is then ready for another measurement. While the use of the disclosure is frequently referred to in a biological or medical context, it will be appreciated that the present disclosure may be practiced in any situation where it is desired to perform in situ chemical analyses of liquid samples at speeds which approach real-time.

A dipstick test device is used for detecting an analyte in a liquid sample such as saliva or other biological fluid by treating the analyte with at least one liquid reagent to form a detectable reaction product. The device can include: a) an aqueous impermeable, aqueous insoluble reaction zone, adapted to retain the detectable reaction product; and b) a control absorbent above, and in liquid-transferring relation with, the reaction zone. The control absorbent can have predetermined, limited liquid-absorbing capacity, and the dipstick is configured for location with a vessel containing the sample. The control absorbent is above the reaction zone, so that the control absorbent fills with sample and the reaction zone incubates with the sample. The device may further include an absorbent reservoir which can move into liquid transferring contact with the reaction zone.

This device and method is for use for detecting an analyte, for example, using an immunoassay. An analyte in a sample may be detected by treating the sample with various reagents, such as labeled immunological binding partners to the analyte and reagents to enable detection of the label. Often, the sample is washed between administrations of various reagents.

An assay may depend on controlling the amount of reactants exposed to the sample and the duration of the reactions taking place. It is desirable to have the ability to assay small sample volumes with relative low concentrations of analyte, and/or to detect relatively small differentials in analyte concentration. Finally, it is desirable to have a system to permit measuring whole blood samples, serum and saliva or other bodily fluid without complex equipment.

One method for adding and washing reagents in an immunoassay uses an absorbent material to move liquid washes and reagents through a solid substrate such as a membrane to which other reactants are immobilized.

There can be an immunoassay test device including sorbent material for drawing liquid through a microporous membrane at the bottom of a test well. The sorbent material is resiliently biased away from the membrane, and it draws liquid through the membrane only when the two are forced together to overcome the bias. Sorbent material comprises a surface layer which is hydrophobic and a bulk portion which is wettable. Reagents are added serially to the test well and, after each reagent has been in the well for a prescribed time, the membrane and sorbent material are forced together to draw off liquid before the next reagent is added.

Generally there is a dipstick test device for detecting an analyte in a liquid sample such as saliva or other biological fluid by treating the analyte with at least one liquid reagent to form a detectable reaction product. The test device includes two components: a) means defining an aqueous permeable, aqueous insoluble reaction zone, adapted to retain the detectable reaction product; and, integral with or separate from the reaction zone, b) a control absorbent above, and in liquid-transferring relation with, the means defining a reaction zone The control absorbent has a predetermined, limited, liquid-absorbing capacity. The dipstick is sized and configured for insertion in a vessel containing the sample, with the control absorbent oriented above the means defining a reaction zone, so that the control absorbent fills to capacity and the means defining a reaction zone incubates with the sample.

The reaction zone comprises at least one reactant e.g., a specific binding partner for the analyte participating in a reaction to form the detectable product.

The reaction product is detected by visual inspection, and the means defining a reaction zone is visible by external inspection of the device; optionally, the device includes a contrast region surrounding the reaction zone to aid in the assay by contrasting with the reaction zone in respect to a characteristic being assayed; also optionally, the device can include an intensity scale for quantitative detection of sample analyte.

The reaction zone is either integral with the control absorbent or it is attached to a face of the control absorbent The reaction zone can define at least two reaction regions, and the test device comprises means for isolating the reaction regions from each other. At least one reaction region may be a control region.

The device includes an aqueous impermeable face plate having at least one opening to allow liquid to reach the means defining a reaction zone. In order to provide a flush test head, the means defining a reaction zone comprises a flat reagent retention element having a node positioned to extend into each face plate opening.

The test may include a reagent pack sized and configured to supply a plurality of reagents to the reaction zone. For example, the reagent pack may include liquid reagents for generating a detectable reaction product.

The reaction zone can be positioned at one end of an elongated dipstick, and the device further can comprise a filter assembly positioned at an end of the dipstick. The device can include a reaction tray comprising a well for the filter assembly on the dipstick and to retain the filter assembly as the dipstick is removed from the well.

Detecting an analyte in a sample is by reacting the analyte with at least one reagent to form a detectable reaction product. The method can include:

a) providing a test device comprising a control absorbent above, and in-transferring relation with, a defined a reaction zone, the control absorbent having a predetermined, limited, liquid-absorbing capacity; the control absorbent is in liquid-transferring relationship with the defined reaction zone;

b) inserting the dipstick into a vessel containing a predetermined volume of sample, with the control absorbent oriented above the defined reaction zone;

c) incubating the predetermined sample volume with the reaction zone;

d) allowing formation of the detectable reaction product; and e) detecting the reaction product.

Different Criteria for Dogs and Cats

For a healthy control dog or cat, the salivary IgA antibody levels are generally below about 10 U/ml (dog) or below about 25 U/ml (cat). The salivary IgM antibody levels are generally below about 25 U/ml for healthy dog or cat.

For a patient dog or cat with moderate food allergy and food intolerance, at the salivary IgA antibody levels are generally at about 15 U/ml (dog) or at about 30 U/ml (cat); The salivary IgM antibody levels are at about 35 U/ml for patient dog or cat.

For a patient dog or cat with severe food allergy and food intolerance, the salivary IgA antibody levels are generally below about 20 U/ml (dog) or about 35 U/ml (cat). The salivary IgM antibody levels are generally at about 40 U/ml (dog or cat).

Most of the readings (about 98%) for the salivary IgA antibody levels in the healthy control dog or cat are under about 10 U/ml (dog) or 25 U/ml (cat). Likewise, most of the readings (about 85%) for the salivary IgM antibody levels in the healthy control dog or cat are under about 25 U/ml. However, there are certain readings in the panel of the healthy control dog or cat that are higher than about 10 U/ml (dog) or 25 U/ml (cat). Particularly higher readings in the healthy control dog or cat may indicate sensitivity to the corresponding dietary antigen.

In the patient dog or cat with moderate food allergy and food intolerance, most of the readings for salivary IgA antibody levels are above about 15 U/ml (dog) and 30 U/ml (cat). In the patient dog or cat with severe food allergy and food intolerance, most of the readings for salivary IgA antibody levels are above 20 U/ml (dog) and 35 U/ml (cat).

The serum antibody can be IgA, IgM, IgG or immune complex. The serum level of at least one of:
 (a) about 100 mg/dl (dog), and about 300 mg/dl (cat) of IgA; or
 (b) about 200 mg/dl (dog) and about 300 mg/dl (cat) of IgM; or
 (c) about 1750 mg/dl (dog) and about 2500 mg/dl (cat) of IgG; or
 or a relative increase in the level of immune complex is indicative of at least mild insensitivity or intolerance.

Many different formats are possible for carrying the sample bodily fluid to the reaction zone. In some cases the bodily fluid is applied to an appropriate filter paper or other carrier material and the filter paper or other carrier material with that fluid sample is impregnated on and in the paper or other carrier material carrier and is then sent to a laboratory by any convenient means for analysis. The paper or other carrier material including the sample may, for instance, in one part contain saliva or other bodily fluid, and in another separate part there can be serum. By using filter paper or other carrier material as the carrier, it can be easy for an owner of a pet to simply mail a sample to a laboratory for appropriate testing of one or more antigens. The filter paper or other carrier material can have one or more reaction zones for different antigens. This carrier system of filter paper or other carrier material permits for a wholly or partly dehydrated sample to be carried to a laboratory for subsequent processing, which can include a hydration step prior to analysis in an appropriate analyzer.

The next or final stage of testing relates to genetic, DNA/RNA or nutrigenomics testing. As such the disclosure is concerned with nutritional genomics or nutrigenomics and nutrigenetics. Such testing in the staged testing procedure is applied generally after either one or both the saliva mucosal fluid or serum testing has been completed, and the results of that testing are inadequate, inconclusive, non-definitive or the patient needs further specificity or accuracy in relation to the food intolerances or sensitivity.

The disclosure includes a method of modulating the regulation of a gene or the protein expression or metabolites in an animal by nutritional management, including the step of analyzing the gene or protein expressions or metabolites. Selected genes, proteins or metabolites in the samples are identified for a particular phenotypic parameter. The effect of a biologically active nutrient varies for different genotypes. A biologically active nutrient is provided to the animal to modulate the selected genes, proteins or metabolites so as to change the response of the animal to the particular phenotypic parameter in a desirable manner.

Typical genes, proteins and metabolites are, for example, those involved in the toxicology and nutrigenomics research (apoptosis, cell cycle, DNA damage signaling pathway, drug metabolism phase I and phase II enzymes, PI3K-AKT signaling pathway, toxicology and drug resistance), cytokines and inflammatory response (inflammatory cytokines and receptors, inflammatory response and autoimmunity, NFKβ signaling pathway, TNF ligand and receptor), metabolic diseases (diabetes, insulin signaling pathway, obesity, oxidative stress and antioxidant defenses) and neurological disorders (depression, epilepsy, general anxiety disorders and panic disorders).

The animals can be selected from livestock, companion, sporting, working and different domesticated pet and laboratory animals, also including fish. These can include for example the following: birds, cat, cattle, dog, donkey, goat, guinea pig, hamster, horse, mouse, pig, poultry, quail, parrots, rabbit, rat, salmon, sheep, trout and turkey or exotic animals.

The phenotypic parameter can be, for example, growth, reproduction, lactation, maintenance, geriatric, inherited and acquired diseases, allergic, arthritic, autoimmune, inflammatory, metabolic and pathopsychological or psychological conditions.

The identification of the selected genes, proteins or metabolites in the sample can be effected by high throughput screening (HTS) techniques, such as microarray, pathway specific microarray, serial analysis of gene expression and gene sequencing. Alternative HTS methods to analyze the sample include proteomic and metabolomic assays.

The term "healthy" is a well defined term. In this application the term refers to an individual animal that has been determined to be well on the basis of physical examination, laboratory data of blood or other biological fluids or tissues, and the information provided by the animal's caregiver, owner or guardian.

The term "unhealthy" is a well defined term. In this application the term refers to an individual animal with physical or physiological or pathological or genetic deviation from the state of health.

The term "biologically active nutrient" in this application refers to a compound or composition or ingredient of an ingested material that has some biological measurable or documented effect in the body of an individual animal.

The method includes identifying a biologically active nutrient based on what is termed the "molecular dietary signature" that the biologically active nutrient induces in an individual animal, the molecular dietary signature being a variation of expression of a set of genes, protein or metabolites which may differ for the genotype of the individual animal.

The molecular dietary signature relates to the interaction between the nutritional environment and genome in an individual in the sense of nutritional genomics or nutrigenomics. The basic concept is that chemical nutrients affect gene expressions in a specific mode switching from health to a pathophysiological condition or vice versa. The advancement of knowledge in human and animal genomes and the spread of biotechnology offer the opportunity to individualize dietary intervention to prevent, mitigate or cure chronic diseases (i.e., individualized nutrition). The concept applies not only to companion pet animals, laboratory animals, but also to nutrient-genome interactions in farm animals. For farm animals, nutrigenomics can be applied for the improvement of productive performances, and the control of infectious and metabolic diseases, through the use of appropriated dietary compositions or supplements.

In companion pet animals, nutrigenomics can be directed to enhancement or maintenance of health and quality of life through the identification of the most suitable diet or supplementation to maintain or optimize the physiological health.

The animal genome and biotechnology systems, such as microarray platforms, can be used to modify the effect of nutrients on gene and protein expression profiles and the adaptation of animals to nutrient exposure, and as a mechanism to identify genetic variants with favorable or unfavorable traits. Nutrigenomics, namely the integration of functional genomics, nutrition, health and biological response, and the regulatory role of nutrients on gene expressions is enabled by microarray technology and integrated on an informatics platform. Nutrigenetics is the retrospective analysis of genetic variations among individuals with regard to their clinical response to specific nutrients.

The high throughput screening technologies are employed to identify a large number of markers or target molecules of a specific parameter treatment or pathology. This is applied to animal or pet nutrition to identify a set of genes, proteins, metabolites or other markers that are unique for a specific intake of each nutrient, chemical compound or xenobiotic. A specific nutrient affects body response in a form that is a molecular dietary signature.

This same concept as applied to gene expressions, measured with microarray technology, leads to the identification of a unique molecular dietary signature for each specific nutrient. In the case of gene expressions, the utilization of a public data repository allows the identification of a set of genes involved in biological processes, molecular function or cellular component, or in a mix of them, which are affected by the dietary change or composition. The three main classifications of gene functions are incorporated in the gene ontology project, which provides a controlled vocabulary to describe gene and gene product attributes in any organism. Other classifications are (KEGG, Kyoto Encyclopaedia of Gene and Genomes; and Biocarta) to identify the unique signature that a dietary change or composition is able to produce in an organism.

The signature of a particular nutrient can also vary from individual to individual, according to the DNA polymorphisms of the genes or genome. In the case that the genetic make-up of the individuals is known, the molecular dietary signature of mutant animals compared to that of wild-type animals forms a family of molecular signatures, which are used for the identification of the action of the nutrient.

EXAMPLE

Compound A is an anti-arthrosis natural plant extract which is fed to a group of 20 dogs, 10 healthy and 10 unhealthy dogs affected by arthrosis. The compound is fed for 15 days. Before and after the period of administration, a blood sample is drawn and used for a transcriptome analysis (gene expression) using a commercial oligomicroarray containing 44000 probes. The number of genes which significantly varied after the treatment is 73, when compared to those of the group of healthy animals that received a placebo.

Data mining using a public domain repository database and software indicated that the 73-gene variation of gene expression involved the Gene Ontology pathway response to stress, external stimuli, immune system process and cell communication. The average number of genes involved in each pathway is 15 (10 up-regulated and 5 down-regulated), 10 (5 up-regulated and 5 down-regulated), 23 (18 up-regulated and 5 down-regulated) and 25 (5 up-regulated and 20 down-regulated), respectively for a total of 73 genes (38 up-regulated and 35 down-regulated). These genes form a distinct cluster molecular dietary signature, which significantly differs from the level of expression of the placebo fed control group of dogs, and represent the action and response of the organism to the dietary compound. No other dietary compounds tested will produce the same molecular dietary signature when administered to dogs.

| Gene Ontology | Up-regulated | Down-regulated | Total |
| --- | --- | --- | --- |
| Response to stress | 10 | 5 | 15 |
| Response to external stimuli | 5 | 5 | 10 |
| Immune system process | 18 | 5 | 23 |
| Cell communication | 5 | 20 | 25 |
| Total | 38 | 35 | 73 |

However, in looking at the individual response for each dog of the group receiving Compound A, some variations occurred. In other words, if the average values are 38 genes up-regulated and 35 genes down-regulated, some of these genes will not change expression levels in some of the dogs receiving compound A. In the example, 5 of 10 dogs respond differently to the dietary administration of compound A.

| Gene Ontology | Up-regulated | Down-regulated | Total |
| --- | --- | --- | --- |
| Response to stress | 8 | 5 | 13 |
| Response to external stimuli | 5 | 2 | 7 |
| Immune system process | 10 | 5 | 15 |
| Cell communication | 4 | 18 | 22 |
| Total | 27 | 30 | 57 |

In the example, genotyping of these dogs indicated that the 5 individuals with a different response to the biologically active compound A presented a single nucleotide polymorphism (SNP) of the canine CYP1A2 gene that results in a deficiency of cytochrome P450 activity. For the biologically active compound A, two molecular dietary signatures are reported, one for each genotype.

There is a method of identifying a biologically active nutrient for an individual animal having a genotype, which comprises:

(a) using a "reference" dataset containing functional genomic profiles of biological samples of the genotypes of different animals of the species, the different animals being healthy animals;

(b) selecting a "target" dataset containing the functional genomic profile of biological samples of the genotypes of different animals, the different animals being unhealthy animals;

(c) using a "biologically active nutrient" dataset comprising different effects of biologically active nutritional components on functional genomic profiles of the different animals of different genotypes from those of the target group (b), the different genotypes being differently responsive to the same biologically active nutritional components; and (d) having the reference dataset or target dataset include an individual animal for which the biologically active nutrient is to be identified.

At least one of the "reference" or "target group" datasets is related with the "biologically active nutrient" dataset to identify a biologically active nutrient for the selected animal genotype to prevent, treat, control, or modulate a state of physiological homeostasis or pathophysiological condition of the individual animal in the reference dataset or target group.

The identification is based on the molecular dietary signature being the expression of a gene or a set of genes which may differ for the genotypes of different animals of the same species. The nutrient identification includes the molecular dietary signature that the biologically active nutrient induces in the individual animal.

The animal can be either a canine or a feline. The canine or feline is from the group consisting of one or more breed type, specific breed, chronological age, physiological age, activity level, healthy, and unhealthy.

The pathophysiological phenotypic conditions can be any one or more examples of any inherited or acquired diseases or conditions such as autoimmunity, anxiety, arthritis, depression, variable body condition score, immune suppression, inflammation, aural disease, skin, aging and behavioral changes, cancer or neoplasia, cardiovascular disease, ocular disease, orthopedic disease, endocrine disease, hematogical disease, kidney disease, gastrointestinal disorders including inflammatory bowel disease (IBD), acute or chronic diarrhea, exocrine pancreatic insufficiency, mal-digestion and pancreatitis, hepatic disorder, liver disease, obesity, dental disease, and pulmonary disease.

The data of the individual animal can be one or more data items related to genotype, including breed, breed(s) of parents, pedigree, sex, coat type, and evident hereditary conditions and disorders. Physiological related conditions include one or more of age, weight, veterinary medical history, reproductive history, health or unhealthy conditions, appetite, physical activity level, mental acuity, behavioral abnormalities and disposition.

The reference data can include one or more data of DNA, RNA, proteins, metabolites and biomarkers selected from an individual animal or groups of animals with different genotypes in physiological homeostasis.

The target group data can include one or more data of DNA, RNA, proteins, metabolites and biomarkers selected from an individual animal or groups of animals with different genotypes in non-physiological homeostasis.

The biologically active nutrient data can include one or more data of DNA, RNA, proteins, metabolites and biomarkers selected from an individual animal or groups of animals with different genotypes, the different genotypes being responsive differently to the same nutritional components.

The data comprise analytical data from a biological sample obtained from an individual animal.

The identified nutrient can be one or more of a food, part of a food, a supplement, a nutraceutical or any biologically active nutrient selected to enhance an aspect of health of an animal. Health can be promoted by preventing, attenuating or eliminating at least one disease state in one or more animals or by restoring physiological homeostasis.

Nutrigenomics is the identification of the appropriate nutrient to modify the phenotype, based on nutrient-inducible genes, nutrigenetics represents the identification of the appropriate nutrient for a defined genotype. Nutrigenetics is an applied science, driven by the paradigms of nutritional pharmacology, the onset of genetic polymorphism, and of clinical experience. Nutrigenomics is a discovery science, driven by the paradigms of molecular biology, enabled by microarray technology, and integrated on an informatics platform.

The role of gene-nutrient interaction is recognized for some monogenic and multi-factorial defects. Monogenic diseases are determined by a single gene and multi-factorial diseases by the combination of several genes with other non-genetic factors. Sometimes, the classification may be an oversimplification, since monogenic diseases also may involve more than a single gene and environmental factors can modulate the expression of phenotype. Some classical monogenic diseases in humans are phenylketunuria, galactosemia, lactose intolerance and celiac disease. In most of the case of monogenic disease, dietary intervention can be used to avoid or treat the patients. In the case of phenylketunuria, an autosomal recessive defect resulting from a deficiency of phenylalanine hydroxylase which leads to mental retardation, a phenylalanine restricted diet avoids the severe consequences of the disease. Similarly, galactosemia, an autosomal defect, is related to the deficiency of one of the three main enzymes involved in galactose metabolism (galactose-1-phosphate uridyltransferase, galactokinase, uridine-diphosphate galactose-4' epimerase), impairing galactose metabolism, resulting in feeding difficulties, and prolonged conjugated hyperbilirubinemia during neonatal life. Avoidance of breast feeding and galactose in the diet prevent the consequences of this defect.

Among the multi-factorial chronic/age-related diseases, cardiovascular diseases, and metabolic syndrome, cancer, osteoporosis and neurological diseases are some classical examples in humans and these syndromes are generally associated with the aging process. Senescence is an obligate fate of cells, but gaining the knowledge of the gene-environment interactions can be effective in reducing the gap between normal and ideal—healthy—aging. Dietary factors are relevant for the onset and progression of degenerative diseases and solid scientific evidence has to be provided to support nutritional intervention. Also the multi-factorial chronic/age related diseases respond in a different way according to the genotype of the individual animal, leading to a so-called "individual susceptibility" or "genetic risk factor".

The disclosure integrates the concepts of nutrigenetics with that of nutrigenomics, considering:

(a) the different genetic make up of individual animals, or a group of them;

(b) the different functional genomic profile for different phenotypic classes of animals (namely healthy, unhealthy, affected, not affected, physiological states, pathophysiological conditions); and (c) the variable response of an individual animal or group of animals to a nutrient.

The "genotypic information" relates to genetic mapping, genetic background, and genetic screening databases. This includes data obtained from the pedigree, family history, heritable physical characteristics, genetic screening tests, DNA testing, genomic mapping, and related laboratory assessment of the gene product for known or suspected congenital and heritable traits. In this application, the term "gene product" means the specific phenotypic characteristic(s) resulting from the expression of the genotype, and may include certain specific laboratory or other test data.

The "genotypic information" typically relates to individual animals, or a group or class of animals. This genotypic information, namely the physical characteristics and genetic makeup (pedigree), heritable disorder history, and related health history of animals in the group is usually manually recorded by breeders, owners, and researchers of companion and other valued animals. The genetic constitution of an individual includes genes without visible effects as well as those revealed by the phenotype. It may refer to all the genes or to a single pair of alleles.

"Genotyping" refers to the process of determining the genotype of an individual by the use of biological assay, such as polymerase chain reaction (PCR), DNA sequencing, and DNA microarrays. The technique provides a measurement of the genetic variation between members of a species and is uses to investigate disease, productive, reproductive and nutrition-associated genes. The most common type of genetic variation is the single nucleotide polymorphisms (SNP) that is a single base pair mutation at a specific locus, usually consisting of two alleles. SNPs are often found to be associated with many diseases, productive and reproductive traits of animals and are becoming of particular interest in pharmacogenetic, pharmacogenomic, nutrigenetic and nutrigenomic studies.

A group of animals of the same specie having the same genotype includes individuals that share a minimum number of common SNPs or other DNA markers that are related to a defined characteristic. In that sense, one animal can be included in several genotype groups, according to the specific characteristic to which that the group relates.

In humans, the use of SNPs is being extended to the haplotype (HapMap project), which is attempting to provide the minimal set of SNPs needed to genotype the human genome. Similar haplotyping is being extended to animals.

SNPs can also provide a genetic fingerprint for use in identity testing.

The "group" can be defined at least in part by a physiological condition that is a product of interaction of the genotype with the environment of an animal or a group of animals. The term "physiological condition" refers to one or more of the physical, behavioral and biochemical attributes of an animal including its size, weight, age, sex, activity level, disposition, and condition of heath or disease.

"Functional Genomic Profile" as used in this disclosure includes DNA regions transcribed into RNA, expressed genes, expressed sequence tag (EST), micro RNA, translated proteins and their derived metabolites. A functional genomic profile can be established using any one or more of a genomic, proteomic or metabolomic approach. A functional genomic profile can result from information from DNA, RNAs, peptides, proteins, or metabolites associated with a phenotypic condition of an animal in response to exposure to one or more biologically active nutrients.

Information for the Functional genomic profile as used in this disclosure is generated from biological samples by any technique known in the art of functional genomics. Examples of techniques useful in generating functional genomic analysis include, without limitation, the following techniques that can be used individually or in combination: (a) DNA, cDNA, RNAs and protein arrays and microarrays in the existing low and high density formats; (b) polymerase chain reaction (PCR) techniques including single and multiplexed quantitative real-time PCR techniques; (c) serial analysis of gene expression (SAGE); (d) DNA and RNA sequencing; (e) Southern blot analysis, Northern blot analysis and Western blot analysis; (f) gel electrophoresis, including two-color 2D gel methodologies, SDS-polyacrylamide gel electrophoresis (SDS-PAGE), and 2D PAGE; (g) protein sequencing, using variable existing mass spectrometry techniques; (h) metabolite analysis, using variable existing mass spectrometry techniques; (i) liquid chromatography by itself or in tandem with mass spectrometry techniques and other separative analytical techniques.

As used in this disclosure, the functional genomic profile extends beyond measurements of clinical pathology analytes such as complete blood count, serum chemistry, hormone assays and analysis.

The functional genomic profile of an animal can be associated with a "normal" or "abnormal" phenotype. A "normal" phenotype is one occurring in an animal exhibiting a condition of health as defined herein, and generally indicative of such a state. A "normal" phenotype is associated with physiological homeostasis, i.e., a tendency to stability of optimal bodily functions. An "abnormal" phenotype is one that is outside the range identified as "normal" and can be associated with a breakdown in physiological homeostasis or pathophysiological condition.

A functional genomic profile from a normal phenotype differs at least in one piece of data or information from the functional genomic profile of an abnormal phenotype. A progressive drift from normality can lead to the death of the individual, requiring an intervention to restore the physiological homeostasis to a healthy, normal condition.

A normal phenotype can present a functional genomic profile generally associated with an abnormal phenotype, indicating a latent non-physiological homeostasis or hereditary predisposition. This drift from the normality requires a preventive or prophylactic intervention to restore the physiological homeostasis to abnormal healthy condition.

"Biological samples" include for instance feces and urine, blood, lymph, tears, cheek swab, saliva, amniotic fluid, serum, prostatic and vaginal secretions, hair, tissue biopsies and necropsy specimens.

The "reference dataset" includes the functional genomic profile of biological samples and genotype information for the animals with normal phenotype, typically stored in digital form and organized in one to a plurality of databases.

The "target group dataset" contains the functional genomic profile of biological samples and genotype information for the animals in abnormal unhealthy conditions.

The "nutrient dataset" comprises genotype information and the different effects of biologically active nutrients on a functional genomic profile of animal of different genotypes.

The different genotypes respond differently to the same nutritional components, and according to the present disclosure, effects of biologically active nutrients on the functional genomic profile can be determined by controlled experiments in animals having different genotypes and exposed to different levels of, and/or different durations of exposure to, one or more biologically active nutrients.

In one embodiment, an alternative testing model of biologically active nutrients is an ex vivo model using tissue explants obtained from an animal of the same species and the same genotypes, and maintained outside the body of the animal.

The nutrition data set can include data not only on chemical or biological entities known as biologically active nutrients but on a variety of materials that have nutritional, or nutraceutical or pharmacological effect. All such materials are considered biologically active nutrients herein if a useful effect on expression of at least one gene, function of at least one protein or production of at least one metabolite is found. In one embodiment, biologically active nutrients of interest herein are materials having GRAS (generally regarded as safe) or equivalent status under U.S. FDA (Food and Drug Administration) regulations or counterpart regulations in other countries, or are eligible for such status. In other embodiments a biologically active nutrient can be a therapeutically or pharmacologically effective compound, e.g., a drug or herbal medicine.

Otherwise, the macronutrients required in a balanced animal diet (protein, carbohydrate, fat and fiber) are considered separately from biologically active nutrients such as those listed above in designing a nutritional formula, as will be discussed below.

Certain biological materials, especially botanical materials, can be considered biologically active nutrients and can, if desired, be included in the nutrition data set. In many of these, a bioactive chemical entity has been identified. Even where a bioactive component is known, other unknown, bioactive components may be present and contribute to the bioactive effect or effects of the biological material.

Examples of macronutrients are set out:

| MACRO-NUTRIENTS |
|---|
| Chicken meat |
| Beef meat |
| Lamb meat |
| Horse meat |
| Turkey meat |
| Bison meat |
| Ostrich or Enu meat |
| Rabbit meat |
| Venison meat |
| Fish, |
| Egg |
| Rice |
| Carrot |
| Pumpkin |
| Peas |
| Beet, sugar pulp |
| Soy hulls |
| Potato |
| Oats |
| Oil, vegetable |

Examples of micronutrients and biologically active nutrients are set out:

| MICRO-NUTRIENTS AND BIOLOGICALLY ACTIVE NUTRIENTS |
|---|
| Leucine |
| Isoleucine |
| Valine |
| Alanine |
| Glutamine |
| Taurine |
| L-Carnitine |
| *Portulaca oleracea* |
| *Andrographis paniculata* |
| *Butea frondosa* |
| *Sylibum marianum* |
| *Echinacea angustifolia* |
| *Curcuma longa* |
| *Eleutherococcus senticosus* |
| *Valeriana officinalis* |
| *Matricaria recutrita* |
| Conjugated linoleic acid |
| Na sulphate |
| Glucosamine HCl |
| *Vaccinum nirillus* |
| Vitamin E |
| Vitamin C |

| MICRO-NUTRIENTS AND BIOLOGICALLY ACTIVE NUTRIENTS |
|---|
| Vitamin B1 |
| Vitamin B2 |
| Di-methylglycine |
| g-orizanol |
| EPA + DHA |
| Green tea polyphenols |

Data defines the genotype and physiological condition of the individual animal for which a diet is designed, and a nutrition product or composition prepared. This includes the functional genomic profile. In order to design the nutritional formula, the input data for an animal is compared with reference data set and target data set to identify the normal or abnormal unhealthy conditions of the individual animal.

The nutrient data set contains the effects of biologically active nutrients on the functional genomic profile of an individual animal with different genotypes. The nutritional formula is computed to incorporate effective amounts of one or more biologically active nutrients according to the specific effects on the functional genomic profile in order to restore the physiological homeostasis. The nutritional formula can be computed as a dietary or nutritional supplement which can be related to, exclude, or include basic energy, protein, metabolic or other nutrient requirements.

Where a nutritional formula, food or composition is generated, the biologically active nutrients and other components can be in any suitable form. For example, components can be expressed in terms of their content in a food composition (e.g., in % or in mg/g, usually on a dry matter basis), in terms of a daily dosage or allowance (e.g., in g/day), or optionally on a live weight basis (e.g., in mg/kg/day). An illustrative nutritional formula, food or nutrient composition can be obtained by the present disclosure and can for instance include any one or more of the exemplary macro-nutrients, micro-nutrients and/or additives set out above. The food composition could be one or more biologically active nutrient formulas selected from the exemplary macro-nutrients, micro-nutrient and/or additives setout above and self contained and/or added as a "sprinkle" supplement in a dry liquid or semi-moist form to an existing regular or specialized or therapeutic diet.

Animals in conditions of health or disease are identified. Each sample is subjected to functional genomic analysis, for example using an established microarray technique, to evaluate a functional genomic profile for the animal that provided the sample, which reflects the genotype, and physiological, and pathophysiological or other condition of the animal at the time the sample was collected.

Biologically active nutrients are tested in one or more animal having different genotypes.

An example of the comprehensive diagnostic testing used in this disclosure are selected examples for diagnostic genetic panels, screens and microarray analysis or other High Through Put systems ("HTS").

The databases of the functional genomic profile and the nutritional data base can be used to assist in resolution of the disease state or condition.

The system and procedure for carrying out the genetic test is, for instance a microarray analysis of DNA or RNA. Thereafter there will be an analysis with a nutritional data base. This is be done by a comparison of the functional genomic profiles as necessary with one or more of the nutritional databases. This disclosure utilizes comprehensive and cumulative data profiling in a novel way over time to allow one to predict the specific nutritional management interventions that will assist in the care and management of the very earliest stages of specific abnormalities or trends that have been identified in the nutrition profile of animals, thereby extending and improving their nutrition and longevity. This is a unique approach to scientifically and medically determining by comprehensive and cumulative laboratory profiling of individual animals and animals within specified defined groups to permit intervention in preventive and management and treatment of general and veterinary medical nutrition care. Specifically, this disclosure directs the outcome of the laboratory profiling to nutritional and nutritional supplement management of the specific identified abnormalities and trends over time to accomplish this goal. This is not only important but also practical because nutritional intervention and management is relatively inexpensive, non-invasive and easily accepted by the pet owner and the veterinary professional making these recommendations.

Food sensitivity and intolerance testing is used co-jointly in determining a feeding regime. The method includes conducting a first testing for food sensitivity or intolerance diagnosis, such that when reporting from a first test, a sensitivity or intolerance to a particular food ingredient or composition, a first food without the ingredient or composition from a first group of foods is prescribed. Usage of the first food is for a first short-time period.

Thereafter a second testing of the animal for food sensitivity or intolerance diagnosis is conducted. The second testing is based upon attenuation of the food sensitivity or intolerance diagnosis by removing the particular food ingredient or composition that was found to be reactive. A second food without the identified particular ingredient or composition is selected from a second group of foods, and additionally a basal food can be prescribed to combine with the second food.

This is described in more detail.

Selected diets which are applicable to the food sensitivity and intolerance testing are arranged for instance in two phases. A dietary and food regime is arranged around these phases.

Phase I Uses Cleansing or Therapeutic Diets

A. Testing: Perform salivary (and/or blood spot) P-O-S diagnostic kit test, or serum testing or testing using heat map DNA/RNA technology B. Select Appropriate diet from 5 options of a first food group is selected to be one of:
1. Liver/GI tract cleansing
2. Anti-Arthritic
3. Anti-Inflammatory
4. Anti-Allergy
5. Vegetarian (for meat protein allergic dogs)
Feed for 4-6 weeks or longer.

C. Repeat salivary (or blood spot) P-O-S test, or serum testing or heat map testing. Should the sensitivity have been attenuated the second food group can be used. This includes a different formulation of a food product, for instance in sprinkles format. These second group products are selected to be one of:
1. Liver/GI tract cleansing
2. Anti-Arthritic
3. Anti-Inflammatory
4. Anti-Allergy
5. Vegetarian (for meat protein allergic dogs)
Additionally a food which is a Basal Healthy Dog Diet is used. Namely, this is in addition to the "sprinkles" formulation that matches diets 1-5 in B.

In certain cases if there is no attenuation, namely a second testing indicates that the B. option needs to be fed for a second 4-6 weeks or longer. The feeding regime of B. is then repeated.

D. Continue on Basal Healthy Dog Diet+matched sprinkle unless a dog starts to be ill. In that event then retest according to A and switch back to B. or change to C. for another 4-6 weeks or longer.

PHASE II Uses Special Needs Diets

E. Testing: Perform salivary (and/or blood spot) P-O-S diagnostic kit test or serum testing using heat map DNA/RNA technology. This is optional.

F. Select desired diet from 5 options:
1. Geriatric
2. Obesity
3. Immune Enhancement
4. Sport
5. Endurance
Feed for 4-6 weeks or longer then repeat Test E (optionally).

G. Thereafter a second food group is used. This includes a different formulation of a food product, for instance in sprinkles format. These second group products are selected to be one of the foods for F.

Switch over to the sprinkle that matches diets F. 1-5. Additionally a food which is a Basal Healthy Dog Diet is used. Namely, this is in addition to the "sprinkles" formulation that matches diets F. 1-5.

H. Continue on Basal Healthy Diet+matched sprinkle—unless dog is doing poorly or becomes ill. If so then retest as in Test E. and switch back to desired diet and sprinkle of F. or G.

I. Alternatively, the Phase I regime of cleansing diets for 4-6 weeks or longer program should be used and followed if needed.

In the specification, there have been disclosed typical preferred embodiments of the disclosure and, although specific terms are employed, they are used in a generic and descriptive sense only and not for purposes of limitation. Some typical embodiments of the disclosure have been described.

For instance, a multi-stage method of diagnosis being obtaining a sample of a saliva; screening the sample of saliva and obtaining a blood sample; preparing serum from the sample; screening the serum sample, and determining a biologically active nutrient in relation to the animal from a molecular dietary signature can be performed in any sequence, and not necessarily the sequence of saliva analysis, serum analysis and biological analysis.

Many more examples, modifications and variations of the disclosure are possible in light of the above teachings. For instance, although the disclosure and the claims indicate specific steps to perform the invention, the steps described are not limited to a particular sequence of performance and in some circumstances two or more of these steps could be undertaken simultaneously. It is therefore to be understood that within the scope of the appended claims the disclosure may be practiced otherwise than as specifically described, and the scope of the disclosure is set out in the claims.

What is claimed is:

1. A method for diagnosing a food sensitivity in a cat followed by determining a biological active food ingredient comprising the steps of screening a sample of saliva from the cat to detect the level of an IgA antibody to a particular food ingredient and an IgM antibody to the particular food ingredient, and measuring the level of the IgA antibody and the IgM antibody by an immunoassay, and wherein the level below a predetermined level of both IgA and IgM antibodies in the sample is indicative of non-sensitivity, the particular food ingredient being selected from the group consisting of wheat, gluten, corn, beef, meat, fish protein, eggs, grains, botanicals, oils from seeds, fish, vegetables, and fruit and determining the biologically active food ingredient, wherein the biologically active food ingredient is selected from the group consisting of wheat, gluten, corn, beef, meat, fish protein, eggs, grains, botanicals, oils from seeds, fish, vegetable, and fruit.

2. The method of claim 1 wherein the level of at least one of about 30 U/ml of IgA is indicative of food sensitivity; or the level of 35 U/ml of IgM is indicative of food sensitivity.

3. The method of claim 1 wherein the level of at least one of:
   (a) about 300 mg/dl of IgA, or
   (b) about 300 mg/dl of IgM is indicative of food sensitivity.

4. The method of claim 1 including obtaining a blood sample;
   preparing serum from the sample; screening the serum sample to detect a semi-quantitative or quantitative level of at least one of a IgA antibody to the particular food ingredient or a IgM antibody to the particular food ingredient.

5. The method of claim 4 wherein, determining the biologically active food ingredient and such determination comprises:
   using a reference dataset containing functional genomic profiles of biological samples for multiple genotypes of different cats;
   using a target group dataset containing functional genomic profiles of biological samples for multiple genotypes of different cats;
   using a nutrient dataset comprising variable effects of nutritional components on a functional genomic profile of cat, different genotypes that are responsive differently to the same nutritional components; and
   relating the reference or target group datasets with the nutrient datasets, to derive the biologically active food ingredient for the cat.

6. A method for diagnosing a food sensitivity in a cat followed by determining a biological active food ingredient comprising the steps of screening a sample of saliva from the cat to detect the level an IgM antibody to the particular food ingredient, and measuring the level of the IgM antibody by an immunoassay, and diagnosing the food sensitivity of the cat based on the level of the IgM antibody, the particular food ingredient being selected from the group consisting of wheat, gluten, corn, beef, meat, fish protein, eggs, grains, botanicals, oils from seeds, fish, vegetables, and fruit and determining the biologically active food ingredient, wherein the biologically active food ingredient is selected from the group consisting of wheat, gluten, corn, beef, meat, fish protein, eggs, grains, botanicals, oils from seeds, fish, vegetable, and fruit.

7. The method of claim 6 including detecting the level of a particular food ingredient IgA antibody to the particular food ingredient, and diagnosing the food sensitivity of the cat based on the level of IgA antibody.

* * * * *